(12) United States Patent
Jaeger et al.

(10) Patent No.: US 7,091,384 B2
(45) Date of Patent: Aug. 15, 2006

(54) PROCESS FOR INCREASING THE SELECTIVITY OF THE HYDROGENATION OF 4,4'-DIAMINODIPHENYLMETHANE TO 4,4'-DIAMINODICYCLOHEXYLMETHANE IN THE PRESENCE OF AN N-ALKYL-4,4'-DIAMINODIPHENYLMETHANE

(75) Inventors: Bernd Jaeger, Darmstadt (DE); Thomas Haas, Frankfurt (DE); Guido Stochniol, Haltern (DE); Christian Lettmann, Essen (DE); Willi Hofen, Rodenbach (DE); Klaus Stadtmueller, Alzenau (DE); Joerg Lotz, Kalbach (DE)

(73) Assignee: Degussa AG, Duesseldorf (DE)

( * ) Notice: Subject to any disclaimer, the term of this patent is extended or adjusted under 35 U.S.C. 154(b) by 70 days.

(21) Appl. No.: 10/516,319

(22) PCT Filed: Jun. 25, 2003

(86) PCT No.: PCT/EP03/06669

§ 371 (c)(1),
(2), (4) Date: Dec. 13, 2004

(87) PCT Pub. No.: WO2004/007425

PCT Pub. Date: Jan. 22, 2004

(65) Prior Publication Data

US 2005/0148797 A1    Jul. 7, 2005

(30) Foreign Application Priority Data

Jul. 10, 2002    (DE) ................. 102 31 119

(51) Int. Cl.
*C07C 209/72*    (2006.01)
(52) U.S. Cl. ..................... 564/451
(58) Field of Classification Search .................. None
See application file for complete search history.

(56) References Cited

U.S. PATENT DOCUMENTS 5,360,934 A    11/1994  Vedage et al.

FOREIGN PATENT DOCUMENTS

| EP | 0 231 788 | 8/1987 |
|----|-----------|--------|
| EP | 0 324 190 | 7/1989 |
| EP | 0 392 435 | 10/1990 |
| EP | 0 476 359 | 3/1992 |
| EP | 0 639 403 | 2/1995 |

*Primary Examiner*—Brian Davis
(74) *Attorney, Agent, or Firm*—Oblon, Spivak, McClelland, Maier & Neustadt, P.C.

(57) ABSTRACT

The invention relates to a process for increasing the selectivity of the hydrogenation of 4,4'-diaminodiphenylmethane (4,4'-MDA) to diaminodicyclohexylmethane (4,4'-HMDA) by catalytic hydrogenation of a mixture containing 4,4'-MDA as the main component and its mono-N-methyl derivative as a secondary component. According to the invention, the hydrogenation is terminated before a conversion of 4,4'-MDA to 4,4'-HMDA of 99% is achieved. Under these conditions, a substantially smaller proportion of the N-methyl-4,4'-MDA is hydrogenated to N-methyl-4,4-HMDA.

10 Claims, No Drawings

PROCESS FOR INCREASING THE SELECTIVITY OF THE HYDROGENATION OF 4,4'-DIAMINODIPHENYLMETHANE TO 4,4'-DIAMINODICYCLOHEXYLMETHANE IN THE PRESENCE OF AN N-ALKYL-4,4'-DIAMINODIPHENYLMETHANE

CROSS REFERENCES TO RELATED APPLICATIONS

This application is a national stage application of International Patent Application No. PCT/EP2003/006669, filed on Jun. 25, 2003, and claims priority to German Patent Application No. 102 31 119.6, filed on Jul. 10, 2002, both of which are incorporated herein by reference in their entireties.

The invention relates to a process for increasing the selectivity of the hydrogenation of 4,4'-diaminodiphenylmethane to 4,4'-diaminodicyclohexylmethane from a mixture of substances which, in addition to 4,4'-diaminodiphenylmethane and optionally its 2,4'- and 2,2'-isomers, also contains N-alkyl derivatives of these substances, particularly N-methyl-4,4'-diaminodiphenylmethane.

4,4'-Diaminodicyclohexylmethane, also known as hydrogenated methylenedianiline or abbreviated as 4,4'-HMDA, is an important building block for the production of isocyanates, which are used in various resins and paints, and a hardener for epoxy resins. 4,4'-HMDA occurs as three configurational isomers, i.e. as trans-trans-, trans-cis and cis-cis. For the field of application in resins and paints, a 4,4'-HMDA with a low content of trans-trans isomers is desired; this content is generally less than 30%, preferably in the range of 15 to about 25%.

4,4'-Diaminodicyclohexylmethane (4,4'-HMDA) can be obtained by a method that is known per se by the catalytic hydrogenation of 4,4'-diaminodiphenylmethane (=4,4'-methylenedianiline=4,4'-MDA). In industrial practice, not pure 4,4'-MDA but a reaction mixture from the production of 4,4'-MDA is used, which additionally contains the isomers 2,4'-MDA and 2,2'-MDA as main components. As a result of their production, these reaction mixtures can also contain additional amino-group-containing polynuclear compounds. In addition, they can contain various N-alkylated compounds of the corresponding aromatic diamines, particularly mono-N-methyl-4,4'-diaminodiphenylmethane in contents of generally 0.05–2%, usually 0.1 to 1%.

The catalytic hydrogenation of 4,4'-MDA to 4,4'-HMDA with hydrogen on a ruthenium-containing, heterogeneous catalyst has been described in several patent applications. In a first version, for example, the equilibrium composition of the mixture of isomers consisting of the three HMDA isomers, containing about 50–55% of the trans-trans isomer, is produced as a result of the selection of the hydrogenation conditions. The product is also known by the term PACM-50. The description of this version can be taken e.g. from U.S. Pat. No. 3,766,272.

Since the separation of the three stereoisomers of HMDA is technically very complex and burdened with high costs, another version is aimed at the direct production of a product mixture with a proportion of 15–25% of the trans-trans isomer, so-called PACM-20. Numerous versions of this process variant are known, which differ primarily in the selection of the catalyst, support material and reaction conditions. Thus, the EP patent 0 324 190 describes that the hydrogenation can be performed at 50 to 350 bar and 100 to 190° C. if the supported catalyst has-a BET surface area in the range of 70 to 280 m²/g and an average pore diameter $d_p$ of 10 to 320 Å, the catalyst contains 0.1 to 5 wt. % ruthenium and the depth of penetration is at least 50 μm.

The U.S. Pat. No. 4,394,523 sets forth a generic process for the production of 4,4'-MDA with a low content of trans-trans isomer, wherein Ru on aluminium oxide is used as the supported catalyst and the hydrogenation is performed under an $H_2$ pressure of at least 36.5 bar in the presence of an aliphatic alcohol and ammonia.

In the generic process according to EP-A 0 231 788, a supported catalyst containing rhodium and ruthenium is used. In the process according to DE-OS 40 28 270, the Ru supported catalyst preferably contains 1 wt. % Ru and additionally compounds of rare earth metals and manganese, and the preferred hydrogen pressure required is in the range of 200 to 400 bar. Finally, EP-A 0 639 403 teaches a version in which the Ru supported catalyst is characterised by a special clay support and the hydrogenation takes place according to the examples under a high $H_2$ pressure of 300 bar. When this process was reproduced under substantially lower hydrogen pressure, it was shown that this only enabled 4,4'-HMDA to be obtained in an inadequate yield.

Consequently, while it is true that the hydrogenation of 4,4'-MDA is a well-known process, a particular problem occurs when, instead of pure 4,4'-MDA, a technical mixture of substances containing this as the main component, such as that resulting from the production of MDA from aniline and formaldehyde, is hydrogenated. Particularly critical is the quantity of mono- or polyalkylated aromatic diamines present, including particularly mono-N-methyl-4,4'-MDA.

Mono-N-methyl-4,4'-MDA is converted to the corresponding N-methylated cycloaliphatic diamine by the hydrogenation process in the same way as 4,4'-MDA. This compound, owing to the physical properties that are similar to the HMDA isomers, can only be separated from the product mixture using very complex apparatus and with a large loss of 4,4'-HMDA yield. This N-methylated cycloaliphatic diamine leads to problems, even in the trace range, if the corresponding diisocyanate is to be produced from the diamine in subsequent processing, e.g. by phosgenation.

Against this background, a version of hydrogenation is desirable in which the non-N-alkylated compounds are preferably selectively hydrogenated from a mixture of substances containing the MDA isomers and N-alkyl MDA.

The U.S. Pat. No. 5,360,934 describes a process in which the corresponding cycloaliphatic amines are produced from mixtures of substances containing various mono- or binuclear aromatic amines, N-alkylated aromatic amines and such compounds. However, no way of hydrogenating only the non-N-alkylated component with high selectivity from a mixture of substances is set forth.

In the process according to EP-A 0,392,435, the hydrogenation of an MDA crude product is described, which can contain oligomers and formamide derivatives of MDA. The hydrogenation is performed in a batch autoclave to complete conversion (99–100%). There is no mention of any influence of the way in which the process is conducted on a selective inhibition of the hydrogenation of N-alkylated compounds of MDA.

In EP 0 355 272 A, the Rh-catalysed hydrogenation of an MDA crude product containing alkyl-substituted aromatic amines is mentioned. It is disclosed that such compounds do not have a negative effect on the hydrogenation of the main component and do not poison the catalyst. There are no references to a selective hydrogenation of the non-N-alkylated aromatic amines.

EP 0 231 788 A teaches a process for the hydrogenation of MDA on a catalyst containing Rh and Ru. In the tests 29–34, a crude MDA containing 0.3% N-methyl-4,4'-MDA is hydrogenated. With full conversion, a product with only a small proportion of high boilers is achieved. The hydrogenation of the N-methyl-4,4'-MDA contained in the crude MDA and the solution of the selectivity problem on which the present invention is based are not dealt with.

Finally, EP 0 001 425-A also teaches the hydrogenation of a crude product containing 4,4'-MDA. It is mentioned that binuclear aromatics are hydrogenated more readily than trinuclear ones, but the hydrogenation problem of the present invention is not addressed.

The object of the present invention is therefore to set forth a process for the catalytic hydrogenation of 4,4'-MDA to 4,4'-HMDA, which leads to the highest possible yield of resulting cycloaliphatic diamines with the highest possible conversion of the aromatic diamines, wherein the hydrogenation product should have the smallest possible proportion of mono- or poly-N-alkyl-substituted cycloaliphatic diamines.

A further object is aimed at modifying the hydrogenation conditions of the process for the hydrogenation of crude MDA which is known per se in such a way that the hydrogenation of N-alkyl derivatives in the crude MDA is at least partially inhibited and thus the selectivity with regard to 4,4'-HMDA is increased.

EP 1 251 119 A1, which is a document according to article 54(3) EPC, pertains to a continuous process for the preparation of diaminodicyclohexylmethane (PACM). It deals with a suspension hydrogenation, wherein MDA is hydrogenated to a conversion of at least 95%, preferably at least 99%. The problem underlying the present application, namely inhibiting the hydrogenation of N-methylated by-products contained in the crude MDA, was not addressed. Accordingly, no technical teaching for solving the problem was disclosed. The preferred embodiment—MDA conversion of at least 99%—given in this document rather leads away from the problem solution of the present application.

A process has been found for the production of 4,4'-diaminodicyclohexylmethane (4,4'-HMDA) by catalytic hydrogenation of a mixture of substances containing 4,4'-diaminodiphenylmethane (4,4'-MDA) as the main component and its mono-N-methyl derivative as a secondary component with increased selectivity with regard to the hydrogenation of 4,4'-MDA in the presence of a heterogeneous hydrogenation catalyst at a temperature in the range of 50 to 220° C. and a hydrogen pressure in the range of 1 to 30 MPa, characterised in that the hydrogenation is terminated before a conversion of 4,4'-MDA to 4,4'-HMDA of 99% is reached.

The process according to the invention is suitable not only for the catalytic hydrogenation of substantially pure 4,4'-diaminodiphenylmethane (4,4'-MDA) with a small proportion of mono-N-methyl-4,4'-diaminodiphenylmethane, but also for the catalytic hydrogenation of reaction mixtures from the production of 4,4'-MDA which, in addition to 4,4'-MDA as the main component, also contain one or more isomeric compounds from the series 2,4'-diaminodiphenylmethane and 2,2'-diaminodiphenylmethane and, resulting from the production, possibly other polynuclear compounds, together with mono- or poly-N-alkylated compounds of the diaminodiphenylmethanes.

A particular advantage of the present invention lies in the fact that, to achieve the objects set, compared with the prior art, neither a particular catalyst nor particular additives, such as ammonia or lyes, are necessary. Surprisingly, the hydrogenation of the N-alkyl-MDAs is successfully inhibited, at least partially, by controlling the conversion of 4,41-MDA so that 4,4'-HMDA is obtainable with a reduced content of N-alkyl-HMDA.

According to a preferred embodiment, the hydrogenation is carried out up to a 4,4'-MDA conversion in the range of about 90 to 98.9, particularly 95 to 98%.

According to a preferred embodiment, those catalysts are selected and the hydrogenation is carried out under those conditions that enable 4,4'-HMDA to be obtained with a trans-trans proportion in the range of 15 to 25%, particularly 18 to 23%. Examples of features can be taken from the following documents:

EP 0 639 403 A2, EP 0 814 098 A2, DE 199 42 813, EP patent application 02 012 040.8, EP 0 873 300 B1, EP 0 066 211 A1, EP 0 324 190 B1.

The hydrogenation takes place at a temperature in the range of 50 to about 220° C., particularly 70 to 190° C. and preferably at 90 to 150° C. The $H_2$ pressure is generally in the range of 1 to 30 MPa, and the pressure particularly amounts to at least 3 MPa. With an appropriate selection of catalyst, particularly Ru supported catalysts with a BET support surface area of less than 70 $m^2/g$, it is possible to hydrogenate under an $H_2$-pressure in the range of 3 to 15 MPa, particularly 5 to 10 MPa.

In relation to the selection of catalyst, reference is made to the prior art already cited. Supported catalysts with ruthenium or rhodium or a Ru/Rh combination as essential active metals and a support material from the series of e.g. activated carbon, inorganic oxides, such as in particular $Al_2O_3$, $SiO_2$, $TiO_2$, $ZrO_2$, ZnO and MgO, and also bentonite, aluminosilicates, kaolins, clays, kieselguhr and diatomaceous earth are preferred.

As is known from the prior art, the specific surface area, the pore distribution and the ratio of the surface area of the active metal to the surface area of the support influence the efficiency of the catalyst, i.e. its activity at different pressures and temperatures, its lifetime and selectivity with regard to the stereoisomers of 4,4'-HMDA. Oxidic supported catalysts with a BET surface area in the range of >30 to <70 $m^2/g$, when more than 50% of the pore volume is formed from macropores (>50 nm) and less than 50% from mesopores (2–50 nm), are particularly preferred. Supports with a BET surface area of less than 30 $m^2$, particularly 0.5 to 10 $m^2/g$, are also highly suitable. The Ru content of the catalyst is generally in the range of 0.1 to 20 wt. %, preferably 0.5 to 10 wt. %.

An embodiment in which the mixture of substances containing MDA and N-methyl-MDA is hydrogenated in a solvent that, for its part, does not as far as possible have an alkylating effect on the amines formed and contained in the reaction mixture, is also preferred. A solvent is preferably used in a quantity of about 10 to 90 wt. %, based on the solution of the aromatic amine to be hydrogenated.

Suitable solvents are e.g. primary, secondary and tertiary mono- or polyhydric alcohols, such as methanol, ethanol, n- and i-propanol, n-, sec.- and tert.-butanol, ethylene glycol, ethylene glycol mono($C_1$–$C_3$)alkyl ether; cyclic ethers, such as tetrahydrofuran and dioxane; alkanes, such as n- and iso-alkanes with 4–12 C atoms, e.g. n-pentane, n-hexane and isooctane, and cyclic alkanes, such as cyclohexane and decalin. Whereas alcohols can in some cases have an alkylating effect, ethers do not exhibit these disadvantages.

A preferred solvent is tetrahydrofuran. Particularly preferably, a reaction mixture in which the crude substance mixture is present in a concentration of 5–30% in tetrahydrofuran is hydrogenated.

The hydrogenation can also be carried out in the presence of ammonia or a primary, secondary or tertiary amine or a polycyclic amine with a bridged N atom. It is usefully ensured by preliminary tests that no undesirable alkylation and/or isomerisation of the 4,4'-HMDA in the direction of a higher trans-trans proportion takes place under the conditions selected.

For continuous hydrogenation, a fixed bed reactor is preferred. The fixed bed reactor can be operated as a bubble column reactor, but a trickle-bed method is preferred. A trickle-bed reactor is preferably used and operated with an LHSV value in the range of 0.1 to 5 $h^{-1}$ (=litres of the reaction solution of the aromatic amine to be hydrogenated per litre of fixed bed catalyst per hour). According to a particularly preferred embodiment of the process according to the invention, a tube bundle reactor is used and this is operated by a trickle-bed method.

By controlling the conversion of 4,4'-MDA to 4,4'-HMDA according to the invention, i.e. terminating the hydrogenation before a conversion of 99% is achieved, it has become possible to minimise the proportion of N-alkylated derivatives of 4,4'-HMDA and its 2,4'- and 2,2'-isomers. By reducing the 4,4'-MDA conversion by a few percent, the content of N-methyl-4,4'-HMDA in the hydrogenated reaction mixture is successfully reduced by a multiple compared with the content of N-methyl-4,4'-MDA contained in the crude MDA.

EXAMPLES

The hydrogenation was performed continuously in a trickle-bed plant consisting of three reactors connected in series, each with a reactor capacity of 2500 ml. The plant consisted of a liquid feed, the reactors and a liquid separator. The reaction temperature was adjusted for each reactor separately using heat transfer medium-oil circulations. The pressure and hydrogen flow were regulated electronically. The solution of the MDA crude mixture in tetrahydrofuran (THF) or in methanol (MeOH), which additionally contained 1% ammonia in the case of methanol as solvent, was metered into the hydrogen stream with a pump and the mixture fed into the top of the first reactor (trickle-bed method). From there it passed through all three reactors in the same way. After the solution had trickled through the reactors, a sample was taken at regular intervals after each reactor. A separate sampling point was provided after each reactor for this purpose.

The crude MDA used was available in two different grades.

Grade A contained 78 wt. % 4,4'-MDA, 11 wt. % 2,4'-MDA, 0.8 wt. % 2,2'-MDA, 9 wt. % polynuclear high boilers and 0.19 wt. % N-methyl-4,4'-MDA.

Grade B contained 97.5 wt. % 4,4'-MDA, 1.7 wt. % 2,4'-MDA and 0.75 wt. % N-methyl-4,4'-MDA.

In example 7 (B 7) and the comparative examples (VB 5–7) the reaction solution was recycled into the reactor several times to determine the concentration profiles of the reactants at higher conversions.

The Ru supported catalysts H 2017 H/D (catalyst A) and B 4245 (catalyst B) from Degussa were used, both 5% ruthenium on aluminium oxide support extrudates with a diameter of 1.1–1.3 mm.

The results of the catalytic hydrogenation of the mixture of 4,4'-MDA and N-methyl-4,4'-MDA to the corresponding cycloaliphatic compounds 4,4'-HMDA and N-methyl-4,4'-HMDA using the catalysts mentioned above can be taken from the table.

The conversion given in the table refers to the conversion of the 4,4'-MDA, 2,4'-MDA and 2,2'-MDA and the intermediates 4,4'-, 2,4'-, 2,2'-diaminocyclohexylphenylmethane participating in the reaction to 4,4'-, 2,4'-, 2,2'-HMDA. Accordingly, a 100% conversion means the hydrogenation of all aromatic double bonds of the three MDA isomers. In addition, the sole conversion of 4,4'-MDA to 4,4'-HMDA is included in the table by analogy. However, no significant difference is apparent compared with the conversion value for all three MDA isomers.

TABLE

| Example (B) Comparative example VB) | Catalyst | Crude MDA grade | Solvent | Concentration of crude MDA [wt. %] | Temperature (° C.) Reactor 1/2/3 | Conversion (%) (2,2', 2,4' and 4,4 isomer) | Conversion (%) (4,4 isomer only) | N-Methyl-4,4'-HMDA (%) | Sampling after proportion of the total reaction path |
|---|---|---|---|---|---|---|---|---|---|
| VB 1 | A | A | THF | 12.5 | 95/100/105 | 99.5 | 99.6 | 0.18 | 3/3 |
| B 1 | A | A | THF | 12.5 | 90/95/100 | 98.4 | 98.5 | 0.15 | 3/3 |
| B 2 | A | A | THF | 12.5 | 95/100/100 | 95.7 | 95.8 | 0.14 | 2/3 |
| B 3 | A | A | THF | 12.5 | 90/95/100 | 90.8 | 91.0 | 0.12 | 2/3 |
| VB 2 | B | A | THF | 12.5 | 95/102/105 | 99.9 | 99.9 | 0.19 | 3/3 |
| B 4 | B | A | THF | 12.5 | 95/100/105 | 97.4 | 97.6 | 0.15 | 3/3 |
| B 5 | B | A | THF | 12.5 | 100/105/110 | 95.0 | 95.4 | 0.13 | 3/3 |
| VB 3 | B | B | THF | 12.5 | 83/98/105 | 98.8 | 98.8 | 0.67 | 3/3 |
| VB 4 | B | B | THF | 12.5 | 83/98/105 | 99.6 | 99.6 | 0.69 | 3/3 |
| B 6 | B | B | THF | 12.5 | 83/98/105 | 95.4 | 95.4 | 0.49 | 2/3 |
| VB 5 | A | A | MeOH | 26 | 105/105/105 | 99.7 | 99.8 | 0.38 | 11/12 |
| VB 6 | A | A | MeOH | 26 | 105/105/105 | 99.5 | 99.5 | 0.21 | 10/12 |
| VB 7 | A | A | MeOH | 26 | 105/105/105 | 99.0 | 99.0 | 0.21 | 8/12 |
| B 7 | A | A | MeOH | 26 | 105/105/105 | 97.0 | 97.0 | 0.16 | 6/12 |

The table shows that a 1.3% reduction in the conversion of MDA to HMDA (from 99.5% in VB1 to 98.4% in B1) brings about more than a proportionally large reduction in the formation of N-methyl-4,4'-HMDA of 16.6% (from 0.18% in VB1 to 0.15% in B1).

The effect according to the invention becomes even clearer when comparing VB 3 and VB 4 with B6. Whereas in VB3, with a conversion of 98.8%, almost all the N-methyl-MDA present was hydrogenated, and even when increasing the MDA conversion to 99.6% (VB 4) no further change could be observed, in B6 with a conversion of 95.4%, only 72% of the N-methyl-MDA was hydrogenated.

The process can even be applied when using a solvent that itself alkylates in traces. VB 6 and VB 7 show here too that, with conversions of >99%, all the N-methyl-MDA is hydrogenated, whereas in B 7 with a conversion of 97.0% only 76% is hydrogenated. If, as in VB 5, the conversion is increased beyond this, a further alkylation of HMDA by the methanol present becomes apparent, even with the simultaneous presence of $NH_3$.

The effect according to the invention can be demonstrated for both catalysts A and B in a similar way. The effect is particularly significant if the conversion of 4,4-MDA' to 4,4'-HMDA is kept within a range of 90% to less than 99%.

The invention claimed is:

1. A process for the production of 4,4'-diaminodicyclohexylmethane (4,4'-HMDA) by catalytic hydrogenation of a mixture comprising 4,4'-diaminodiphenylmethane (4,4'-MDA) as the main component and a mono-N-methyl derivative thereof as a secondary component with increased selectivity with regard to the hydrogenation of 4,4'-MDA in the presence of a heterogeneous hydrogenation catalyst at a temperature in the range of 50 to 220° C. and a hydrogen pressure in the range of 1 to 30 MPa,
wherein
the hydrogenation is terminated before a conversion of 4,4'-MDA to 4,4'-HMDA of 99% is achieved.

2. The process according to claim 1,
wherein
a crude MDA, comprising at least 70 wt. % 4,4'-diaminodiphenylmethane and 0.01 to 2 wt. % N-methyl-4,4'-diaminodiphenylmethane, is used as said mixture.

3. The process according to claim 2,
wherein
said mixture comprises 75–99 wt. % 4,4'-MDA, 1–11 wt. % 2,4'-MDA, less than 2 wt. % 2,2'-MDA and up to 1 wt. % N-methyl-4,4'-MDA.

4. The process according to claim 1,
wherein
the hydrogenation of 4,4'-diaminodiphenylmethane to 4,4'-diaminodicyclohexylmethane is terminated at a conversion in the range of 90% to 98.9%.

5. The process according to claim 1, wherein the hydrogenation is performed at a temperature in the range of 90 to 150° C. and a pressure in the range of 5 to 15 MPa.

6. The process according to claim 1, wherein an Ru-supported catalyst with an Ru content of 0.5 to 10 wt. % is used.

7. The process according to claim 6, wherein an Ru-aluminium oxide or Ru-titanium dioxide supported catalyst is used as the Ru supported catalyst, the support having a BET surface area of less than 70 $m^2$/g.

8. The process according to claim 1, wherein the catalytic hydrogenation is performed in the presence of a solvent from the series of the ethers.

9. The process according to claim 1, wherein the catalytic hydrogenation is performed in a continuous operating method in a fixed bed reactor packed with an Ru supported catalyst, wherein the reactor is operated by a trickle-bed method.

10. The process according to claim 8, wherein the catalytic hydrogenation is performed in a continuous operating method in a fixed bed reactor packed with an Ru supported catalyst, wherein the reactor is operated by a trickle-bed method.

* * * * *

UNITED STATES PATENT AND TRADEMARK OFFICE
CERTIFICATE OF CORRECTION

| | | |
|---|---|---|
| PATENT NO. | : 7,091,384 B2 | Page 1 of 1 |
| APPLICATION NO. | : 10/516319 | |
| DATED | : August 15, 2006 | |
| INVENTOR(S) | : Bernd Jaeger et al. | |

It is certified that error appears in the above-identified patent and that said Letters Patent is hereby corrected as shown below:

Column 4, line 2, "4,41-MDA" should read --4,4'-MDA--

Signed and Sealed this

Ninth Day of January, 2007

JON W. DUDAS
*Director of the United States Patent and Trademark Office*